United States Patent [19]

Krimm et al.

[11] 3,979,462

[45] Sept. 7, 1976

[54] CONDENSATION RESINS OF PHENOLS AND $\alpha,\alpha'$-DIHYDROXY-DIISOPROPYL BENZENES

[75] Inventors: Heinrich Krimm; Hans-Josef Buysch, both of Krefeld-Bockum; Dieter Freitag, Krefeld, all of Germany

[73] Assignee: Bayer Aktiengesellschaft, Germany

[22] Filed: Dec. 2, 1975

[21] Appl. No.: 636,921

Related U.S. Application Data

[63] Continuation of Ser. No. 461,092, April 15, 1974, abandoned.

[30] Foreign Application Priority Data

Apr. 19, 1973 Germany............................ 2320008

[52] U.S. Cl. .......................... 260/619 B; 260/619 R
[51] Int. Cl.$^2$.......................................... C07C 39/12
[58] Field of Search ......... 260/619 R, 619 A, 619 B

[56] References Cited

UNITED STATES PATENTS

| | | | |
|---|---|---|---|
| 3,232,993 | 2/1966 | Vitrone........................... | 260/619 R |
| 3,251,805 | 5/1966 | Schnell et al..................... | 260/619 B |
| 3,256,347 | 6/1966 | Casate et al..................... | 260/619 B |
| 3,293,213 | 12/1966 | Barton et al. ................... | 260/619 B |
| 3,393,244 | 7/1968 | Brodinek et al................. | 260/619 B |
| 3,689,572 | 9/1972 | Ruppert et al. ................. | 260/619 B |
| 3,758,597 | 9/1973 | Baysch et al..................... | 260/619 R |

*Primary Examiner*—Norman Morgenstern
*Attorney, Agent, or Firm*—Connolly and Hutz

[57] ABSTRACT

A process for the production of light colored condensation resins, wherein phenols are reacted with $\alpha,\alpha'$-dihydroxy-diisopropyl benzenes in the presence of acids of phosphorus at temperatures of between 70° and 270°C.

5 Claims, No Drawings

CONDENSATION RESINS OF PHENOLS AND α,α'-DIHYDROXY-DIISOPROPYL BENZENES

CROSS REFERENCE TO RELATED APPLICATION

This application is a continuation of application Ser. No. 461,092, filed Apr. 15, 1974, and now abandoned.

This invention relates to light coloured resins produced by condensation of phenols and α,α'-dihydroxy-diisopropyl benzenes.

It is known that phenols can be reacted with α,α'-dihydroxy-diisopropyl benzenes to form α,α'-bis-(hydroxyphenyl)-diisopropyl benzenes. This reaction is either catalysed with acids or is carried out at elevated temperatures without catalyst. In the former case, the highly crystalline, difficulty soluble p-alkylated phenols are mainly obtained and in the latter case readily soluble isomeric mixtures of α,α'-bis-(hydroxyphenyl)-diisopropyl benzenes which solidify like resins. Both groups of substances are suitable for preparing resols and resites. The p-alkylated phenols produce crystallisable resols whereas the isomeric mixtures give rise to resinous resols which are readily miscible with other resins such as epoxy resins and polyester resins. Silver lacquers are obtained when these resols are used for coatings, for example as stoving lacquers for metals. In order to obtain such a light colour, however, the crude bisphenols must first be purified either by recrystallization or by distillation.

It is an object of this invention to provide a process for producing the above mentioned hydroxyl compounds in such a way that they can be used without first being carefully purified for the production of resols which have exceptionally valuable properties.

It has been found that by reacting phenols with α,α'-dihydroxy-diisopropyl benzenes or with derivatives thereof which are analogous in their reactions, at temperatures of between 70° and 270°C and in the presence of acids of phosphorus as catalysts, non-crystallising, exceptionally light coloured resinous condensation products are obtained.

Owing to their light colour, these resins can be immediately converted into resol resins of the quality necessary for silver lacquers without the need for first being purified by difficult methods such as high vacuum distillation or treatment with decolourising adsorbents.

The resol resins obtained from the products according to the invention surprisingly have excellent flow properties so that the lacquer films when stoved are practically free from the formation of craters which normally occur when phenol resins are stoved. Furthermore, the resistance of the coatings to chemicals such as organic acids and compounds which split off sulphur is higher than has ever been attained before. The resol resins prepared from the new condensation resins are therefore superior in quality to any previously known in this field.

The resins according to the invention consist essentially as determined by analytical methods of distillation and gas-chromatography of isomeric mixtures of α,α'-bis-(hydroxyphenyl)-diisopropyl benzenes, tetranuclear compounds and higher condensation products whose structure is not accurately known. The sum of the two last mentioned groups of substances amounts to between 30 and 60 % by weight of the products of the process. The phenolic hydroxyl group content of the products is 6.2–8.5 % by weight.

In the British patent specification No. 932,811 it is proposed to use orthophosphoric acid as a catalyst among numerous other acids for the preparation of α,α'-bis-(4-hydroxyphenyl)-diisopropyl benzenes, in other words to prepare pure p-alkylated bisphenols from phenol and α,α'-dihydroxydiisopropyl benzene. The experiments described in the said Patent Specification, however, were carried out either with $BF_3$-etherate at room temperature or with dry HCl gas at 100°C. Our own experiments have shown that the temperature range of −10°C to 150°C indicated in the said patent specification may be valid when gaseous HCl is used as catalyst for the preparation of pure α,α'-bis-(4-hydroxyphenyl)-diisopropyl benzenes but not when orthophosphoric acid is used as catalyst. In any case, at temperatures above 70°C orthophosphoric acid no longer catalyses the formation of pure p-alkylated bisphenols but catalyses the formation of hard resins which have a completely different and unexpected composition and structure. The said Patent Specification also fails to mention the brightening effect of phosphoric acid when it is used under the conditions according to the invention.

Suitable starting materials for preparing the resins according to the invention are phenols which contain at least two free ortho- or para-positions, such as phenol itself, o-, p- and m-cresol, m-isopropyl phenol, 3,5-xylenol, 3,5-diisopropyl phenol and mixtures of these compounds, and diisopropyl benzene compounds such as α,α'-dihydroxy-p-diisopropyl benzene, α,α'-dihydroxy-m-diisopropyl benzene, α-hydroxy-isopropyl-m- and -p-isopropenyl benzene, m- and p-diisopropenyl benzene, α,α'-bis-methoxy-m- and -p-diisopropyl benzene and other alkoxy-diisopropyl benzenes, α,α'-dihydroxy-diisopropyl benzenes which are substituted in the nucleus such as 3-isopropyl-α,α'-dihydroxy-m-diisopropyl benzene and mixtures of these compounds in particular mixtures of α,α'-dihydroxy-m- and -p-diisopropyl benzene.

Suitable catalysts are acids of phosphorus, for example orthophosphoric acid, metaphosphoric acid, pyrophosphoric acid, phosphorous acid and hypo-phosphorous acid. These acids are preferred, although phosphoric acids which are substituted with organic groups, such as phenyl- and alkyl-phosphonic acids and partially esterified acids of phosphorus such as monophenyl phosphate and monocresyl phosphate and acid salts of phosphoric acids such as ammonium dihydrogen phosphate or sodium dihydrogen phosphate are also suitable. The quantity of catalyst used may be between 0.01 and 10% by weight and is preferably 0.05 to 5% by weight, based on the total quantity of reaction mixture. The molar ratio of the reactants is not particularly critical but the phenolic reactant must be used in excess. The molar ratio of phenols to dihydroxy-diisopropyl benzenes used is in the range of about 4:1 to 15:1. Although ratios outside these values may be employed, working up of the reaction product is then more difficult.

The reaction temperature employed is between 70° and 270°C, preferably between 80° and 220°C.

A simple method of carrying out the process consists of boiling the reaction mixture under reflux either in the presence of the water produced by the condensation or after this has been removed by azeotropic distillation. The reaction time is also not critical and is between 1 and 8 hours, preferably between 2 and 5 hours. The reaction may be carried out with or without solvent and is preferably carried out under an inert gas such as nitrogen as protection against oxidation.

The catalyst is normally neutralised after the condensation reaction, for example by adding an equivalent quantity of sodium or potassium hydroxide solution. Isolation of the condensation resins is preferably carried out by distilling off the excess phenol under reduced pressure. The resins are immediately ready for use for the preparation of resols, epoxide or polyester resins.

Preparation of the resols is carried out by heating the inventive condensation resins dissolved in an alcohol which contains 1 to 4 carbon atoms with a 30–35 % aqueous solution of formaldehyde or formaldehyde donors such as paraformaldehyde and a basic catalyst or by heating the alcoholic solution of the inventive condensation resin with formaldehyde and a basic catalyst which may be added before or during the heating process.

The reaction temperature is between 30° and 140°C, preferably 50°–117°C.

The reaction time depends on the reaction temperature and quantity of catalyst used. It is generally between about 10 minutes and 48 hours. The proportion by weight of formaldehyde (100 %) to condensation resin may be between 1 : 8 and 1 : 1. The catalysts used may be a base such as lithium hydroxide, potassium hydroxide, sodium hydroxide, calcium hydroxide, ammonia or sodium hydroxide together with sodium formate, sodium and potassium carbonate and barium hydroxide and mixtures of any of these catalysts. The quantity of catalysts may be between 0.01 and 2.5 mol for every 350 g of inventive condensation resin used.

Working up of the resol reaction mixture is extremely simple. The reaction mixture is neutralised with a dilute acid such as sulphuric acid, hydrochloride acid, phosphoric acid benzoic acid, acetic acid or lactic acid and concentrated by evaporation or the organic phase is separated after the addition of water and then concentrated by evaporation under vacuum until it has the desired viscosity.

To harden the resol to the resite, a solution of the resol with or without the addition of an epoxy resin (such as Epikote 1007 manufactured by Shell) in a typical lacquer solvent such as methanol, butanol, isobutanol, benzene/butanol, ethyl acetate, xylene or methyl ethyl ketone is applied as a thin film to a metal surface. The usual levelling agents may be added to the solution. By heating the solution to 100°–300°C, preferably 120°–200°C, an insoluble lacquer which has the properties indicated above is obtained. Hardening may also be carried out in the presence of catalytic quantities of acids such as hydrochloric acid, phosphoric acid, oxalic acid, p-toluene sulphonic acid, boric acid or lactic acid. Hardening may also be carried out in a mixture with melamine resins, polyester resins or polycarbonates, with or without acid.

A suitable resin, may for example, be prepared by the following method. 16.95 kg of 49% aqueous sodium hydroxide solution are dissolved in 97.1 kg of 30% aqueous formaldehyde solution at 60°–70°C. This solution is pumped into a solution of 72 g of condensation resin (7.5% of phenolic OH, prepared from a mixture of 60 parts of $\alpha,\alpha'$-dihydroxy-1,3-diisopropyl benzene and 40 parts of $\alpha,\alpha'$-dihydroxy-1,4-diisopropyl benzene and phenol in the presence of phosphoric acid) and 145.5 kg of butanol in the course of 10 minutes at 90°C. The reaction mixture is then stirred for 30 minutes at 90°–93°C. After it has cooled to about 40°C, a solution of 10.1 kg of concentrated phosphoric acid and 150 kg of water is added and the phases are then separated at about 40°C. The organic phase is washed with water and concentrated by evaporation. About 128 kg of resol resin with a solids contents of 63–70% are obtained.

The colour indeces given in the following examples are taken from the iodine scale and determined on 50% solutions of the resins in n-butanol.

EXAMPLE 1

A mixture of 194 g (1 mol) of $\alpha,\alpha'$-dihydroxy-p-diisopropyl benzene, 1130 g (12 mol) of phenol and 4 g of metaphosphoric acid is melted under an atmosphere of nitrogen and heated so that the water produced by the reaction is distilled off over a steam heated reflux condenser. Elimination of water begins when the reaction temperature reaches 125°C and is completed at about 180°–185°C which is the reflux temperature of phenol. After a reaction time of 6 hours, starting from the time of water elimination, 2 g of powdered sodium hydroxide are added, the reaction mixture is left to cool slightly and after removal of the reflux condenser the excess phenol is distilled off at a reaction temperature of up to 210°C and a pressure below 10 mm Hg. 284 g of a pale hard resin which is slightly cloudy due to its salt content are obtained. The colour index is 0. The phenolic OH-content is 8.3%.

EXAMPLE 2

A mixture of 194 g (1 mol) of $\alpha,\alpha'$-dihydroxy-m-diisopropyl benzene, 752 (8mol) of phenol and 4 g of pyrophosphoric acid is reacted in a manner analogous to example 1 and then worked up after the addition of 1.8 g of powdered sodium hydroxide. 260 g of a cloudy, light-coloured hard resin is obtained which has a phenolic OH-content of 7.3% and a colour index of 0.

EXAMPLE 3

A mixture of 136 g (0.7 mol) of $\alpha,\alpha'$-dihydroxy-m-diisopropyl benzene, 58 g (0.3 mol) of $\alpha,\alpha'$-dihydroxy-p-diisopropyl benzene, 752 g (8 mol) of phenol and 1.2 ml of 85 % phosphoric acid is reacted for 4 hours in a manner analogous to example 1. After the addition of 1.2 ml of concentrated sodium hydroxide solution, the excess phenol is distilled off as in example 1, the residue is dissolved in chlorobenzene, and the solution is shaken with water, dried over sodium sulphate and concentrated by evaporation. 260 g of a clear, light-coloured hard resin which has a phenolic OH-content of 7.6 % and a colour index of 0 are obtained in this way.

50 g of the resin is distilled in a high vacuum. 25 g of a fraction consisting of a mixture of isomers of $\alpha,\alpha'$-bis-(hydroxyphenyl)-diisopropyl benzene distil over at 200°–240°C/0.04 mm Hg and 18 g distil over at 240°–320°C/0.04 mm Hg. The residue amounts to 6 g.

EXAMPLE 4

A mixture of 116 g (0.6 mol) of $\alpha,\alpha'$-dihydroxy-m-diisopropyl benzene, 78 g (0.4 mol) of p-di-$\alpha$-hydroxyisopropyl benzene, 940 g (10 mol) of phenol and 4 g of phosphorus acid is reacted for 4 hours as described in example 1. After the addition of 2 g of powdered sodium hydroxide, the reaction mixture is worked up as described in example 3. 284 g of a clear, light hard resin is obtained which has a phenolic OH-content of 8.2% and a colour index of 0.

EXAMPLE 5

A mixture of 116 g (0.6 mol) of $\alpha,\alpha'$-dihydroxy-m-diisopropyl benzene, 78 g (0.4 mol) of $\alpha,\alpha'$-dihydroxy-p-diisopropyl benzene, 752 g (8 mol) of phenol and an aqueous hydrolysate which has been obtained by pouring 3 g of phosphorus trichloride on 10 g of ice is reacted and worked up as described in example 4. 295 g of a clear, pale hard resin is obtained which has a phenolic OH-content of 8.5 % and a colour index of 0.

EXAMPLE 6

A mixture of 116 g (0.6 mol) of $\alpha,\alpha'$-dihydroxy-m-diisopropyl benzene, 78 g (0.4 mol) of $\alpha,\alpha'$-dihydroxy-p-diisopropyl benzene, 752 g (8 mol) of phenol and 10 ml of 85% phosphoric acid is heated to a reaction temperature of 80°C under reduced pressure with stirring while the water produced in the reaction is distilled off. After a reaction time of 2 hours, the water is removed and the pressure reaches 25 mm Hg. After a further 6 hours, 8.8 ml of concentrated sodium hydroxide solution are added and the phenol is distilled off at 210°C and 10 mm Hg. The residue is dissolved in toluene and the solution is freed from the salt by suction filtration. After evaporation of the solution, 262, g of a clear, plate hard resin is obtained which has a phenolic OH-content of 7.5 and a colour index of 0.

50 g of the resin is distilled in a high vacuum. 24.5 g of a fraction which distils over at 210°–240°C/0.05 mm. Hg, are obtained. This fraction consists of a mixture of isomers of $\alpha,\alpha'$-bis-(hydroxyphenyl)-diisopropyl benzene. In addition 13.5 g of a fraction which distils over at 250°–320°C/0.05 mm. Hg. and 11 g of residue which cannot be distilled are obtained.

EXAMPLE 7

A mixture of 116 g (0.6 mol) of $\alpha,\alpha'$-dihydroxy-m-diisopropyl benzene, 78 g (0.4 mol) of $\alpha,\alpha'$-dihydroxy-p-diisopropyl benzene, 756 g (7 mol) of a 70:30 mixture of m-cresol and p-cresol and 1.4 ml of 85% phosphoric acid are reacted for 4 hours as described in example 1. 1.23 ml of concentrated sodium hydroxide solution are added and the reaction mixture is then worked up as in example 1. 262 g of a pale hard resin which has a phenolic OH-content of 63% and a colour index of 0 are obtained.

EXAMPLE 8

A mixture of 1250 g of phenol, 194 g of 7 : 3 mixture of $\alpha,\alpha'$-dihydroxy-m-diisopropyl benzene and $\alpha,\alpha'$-dihydroxy-p-diisopropyl benzene and 2 g of 85 % phosphoric acid is heated to a temperature of 120°–5°C under nitrogen with stirring. After 2 hours, the water of reaction has distilled off as an azeotropic mixture and the sump has reached a temperature of 180°C which is maintained for 2 hours. After cooling to about 100°C, the reaction mixture is neutralised with 4 g of 50% sodium hydroxide solution and the excess phenol is distilled off. 260 g of a yellowish condensation resin which has a phenolic OH-content of 7.3 % and an iodine colour number of 2 are obtained.

EXAMPLE 9

The same mixture as described in example 8 is used except that it contains 4 g of ammonium dihydrogen phosphate as catalyst instead of phosphoric acid. The reaction is carried out as described in example 8 except that the mixture is left to react for 5 hours instead of 2 hours at 180°C. Working up the reaction product yields 231 g of a pale condensation residue which has an iodine colour number of 2.

EXAMPLE 10

When example 9 is repeated but using diammonium hydrogen phosphate as catalyst, 235 g of a pale condensation resin which has an iodine colour number of 3 are obtained.

EXAMPLE 11

When example 9 is repeated but using 2 g of hydrazinedihydrogen phosphate as catalyst, 232 g of an almost colourless condensation resin which has an iodine colour number of 1 are obtained. A 50 g sample of the resin is distilled in a high vacuum. 5.2 g of a fraction which distils over at 161 –205°C/0.1 mm. Hg, 20.8 g of a mixture of isomers of $\alpha,\alpha'$-bis-(hydroxyphenyl)diisopropyl benzene, (205°–245°C/0.1 mm. Hg) and 24 g of residue are obtained.

EXAMPLE 12

A mixture of 3 tons of phenol, 562 kg of a 3:2 mixture of $\alpha,\alpha'$-dihydroxy-m-diisopropyl benzene and $\alpha,\alpha'$-dihydroxy-p-diisopropyl benzene and 6.35 kg of 75% phosphoric acid are heated in a vessel with stirring under nitrogen. Water and phenol begin to distil off as an azeotropic mixture over a distillation column from 131°C onwards. After 3 hours, the reaction temperature has reached 180°–183°C. It is kept at this temperature for about 4 hours and then cooled to about 100°C. 11.2 kg of 50% sodium hydroxide solution are added and the excess phenol is distilled off at 10 mm. Hg. The sump temperature is finally raised for a short time to 220°C while a slow stream of carrier gas is passed through to distil off any remaining phenol. 790 kg of a pale yellow hard resin are obtained. This resin has a phenolic OH-content of 8%, a residual phenol content of less than 0.1% by weight and a colour index of 2 (35% solution in butanol).

COMPARISON EXAMPLE 1

A mixture of 136 g (0.7 mol) of $\alpha,\alpha'$-dihydroxy-m-diisopropyl, 58 g (0.3 mol) of $\alpha,\alpha'$-dihydroxy-p-diisopropyl benzene 940 g (10 mol) of phenol and 1.5 g of p-toluene sulphonic acid is reacted in a manner analogous to example 1. Water begins to split off at a reaction temperature of 135°C. The reaction time is 6 hours. The reaction mixture is then neutralised with 0.35 g of powdered sodium hydroxide and the excess phenol is removed by vacuum distillation. 239 g of a completely opaque, chocolate-coloured hard resin are obtained.

COMPARISON EXAMPLE 2

The previous experiment is repeated but using 20 g of an acid-activated alumina (Tonsil optimum) instead of p-toluene sulphonic acid. 235 g of a pitch-black hard resin are obtained.

COMPARISON EXAMPLE 3

A solution of 194 g of $\alpha,\alpha'$-dihydroxy-p-diisopropyl benzene in 440 g phenol was introduced in the course of about 30 minutes at 80°C into 500 g of phenol which had been saturated with HCl gas, and the mixture was kept at 80°C while treatment with gaseous HCl was continued for 4 hours. After removal of excess phenol by distillation, 340 g of a brown crystalline substance remained behind which according to gas-chromatographic analysis consisted to an extent of 92.6% of α,α'-bis-(4-hydroxyphenyl)-p-diisopropyl benzene.

We claim:

1. A product produced by the process which comprises reacting phenol with a mixture of α,α'-dihydroxy-m-diisopropyl benzene and α,α'-dihydroxy-p-diisopropyl benzene, said dihydroxy compounds being in a molar ratio of between 7:3 and 3:7, in the presence of a catalytic amount of an acid catalyst selected from the group consisting of phosphoric acid, o-phosphoric acid, m-phosphoric acid, pyrophosphoric acid, phosphorous acid and hypophosphorous acid at a temperature of between about 70 and 270°C.

2. The product of claim 1 wherein said catalyst is phosphoric acid.

3. The product of claim 1 wherein said catalyst is phosphorous acid.

4. The product of claim 1 wherein the molar ratio of phenol to dihydroxy mixture is 4:1 to 15:1.

5. The product of claim 1 wherein said catalytic amount is from 0.01 to 10% by weight based on the weight of the total reaction mixture.

* * * * *